(12) United States Patent
Hon (10) Patent No.: US 10,736,357 B2
(45) Date of Patent: Aug. 11, 2020

(54) ELECTRONIC CIGARETTE LIQUID DETECTION AND MEASUREMENT SYSTEMS

(71) Applicant: FONTEM HOLDINGS 1 B.V., Amsterdam (NL)

(72) Inventor: Lik Hon, Beijing (CN)

(73) Assignee: FONTEM HOLDINGS 1 B.V., Amsterdam (NL)

( * ) Notice: Subject to any disclaimer, the term of this patent is extended or adjusted under 35 U.S.C. 154(b) by 390 days.

(21) Appl. No.: 15/538,192

(22) PCT Filed: Dec. 25, 2014

(86) PCT No.: PCT/CN2014/094908
§ 371 (c)(1),
(2) Date: Jun. 20, 2017

(87) PCT Pub. No.: WO2016/101202
PCT Pub. Date: Jun. 30, 2016

(65) Prior Publication Data
US 2017/0340009 A1    Nov. 30, 2017

(51) Int. Cl.
*A24F 47/00* (2020.01)
*A61M 15/06* (2006.01)
(Continued)

(52) U.S. Cl.
CPC .......... *A24F 47/008* (2013.01); *A24B 15/167* (2016.11); *A61M 15/06* (2013.01);
(Continued)

(58) Field of Classification Search
None
See application file for complete search history.

(56) References Cited

U.S. PATENT DOCUMENTS 4,194,395 A * 3/1980 Wood ................ G01F 23/263
361/284
5,017,909 A * 5/1991 Goekler ............ G01F 23/265
340/620

(Continued)

FOREIGN PATENT DOCUMENTS

CN    102865905 A    1/2013
CN    102928048 A    2/2013
(Continued)

OTHER PUBLICATIONS

European Patent Office, "Extended European Search Report", for European Application No. 14908770.2, dated Jul. 25, 2018.
(Continued)

*Primary Examiner* — Thor S Campbell
(74) *Attorney, Agent, or Firm* — Perkins Coie LLP; Kenneth H. Ohriner (57) ABSTRACT

An electronic cigarette or similar vaporization devices include a liquid which is vaporized or atomized in an atomizer. An e-liquid detection system can verify that the e-liquid is acceptable for use in the device. The e-liquid detection system may detect one or more indicators, and/or physical or chemical properties of the e-liquid. The e-liquid detection system may also measure the e-liquid level in the device.

15 Claims, 11 Drawing Sheets

(51) Int. Cl.
*A24B 15/167* (2020.01)
*F22B 1/28* (2006.01)
*G01F 23/292* (2006.01)
*A61M 15/00* (2006.01)
*G01N 21/64* (2006.01)

(52) U.S. Cl.
CPC ............ *F22B 1/284* (2013.01); *G01F 23/292* (2013.01); *A61M 15/0081* (2014.02); *A61M 2205/3306* (2013.01); *A61M 2205/3317* (2013.01); *A61M 2205/3375* (2013.01); *A61M 2205/3386* (2013.01); *A61M 2205/3389* (2013.01); *A61M 2205/3393* (2013.01); *A61M 2205/502* (2013.01); *A61M 2205/6018* (2013.01); *G01N 21/64* (2013.01)

(56) References Cited

U.S. PATENT DOCUMENTS

| | | | | |
|---|---|---|---|---|
| 5,388,594 | A | 2/1995 | Counts et al. | |
| 5,437,184 | A * | 8/1995 | Shillady | G01F 23/266 73/304 C |
| 5,498,855 | A * | 3/1996 | Deevi | A24F 47/008 131/194 |
| 6,155,268 | A * | 12/2000 | Takeuchi | A24F 47/008 131/273 |
| 6,490,920 | B1 * | 12/2002 | Netzer | G01C 9/06 324/687 |
| 6,564,630 | B1 * | 5/2003 | Klemp | G01F 23/266 73/290 R |
| 6,652,495 | B1 * | 11/2003 | Walker | A61L 2/0088 604/317 |
| 7,318,344 | B2 * | 1/2008 | Heger | G01F 23/265 340/612 |
| 7,432,725 | B2 * | 10/2008 | Sieh | G01F 23/268 324/662 |
| 8,931,340 | B2 * | 1/2015 | Wiederkind-Klein | G01F 23/268 73/304 C |
| 9,261,395 | B2 * | 2/2016 | Shearer | G01F 23/268 |
| 9,605,990 | B2 | 3/2017 | Enomoto et al. | |
| 9,833,019 | B2 * | 12/2017 | Ampolini | A24F 47/008 |
| 10,070,662 | B2 * | 9/2018 | Gorilovsky | A24B 15/167 |
| 2005/0007239 | A1 | 1/2005 | Woodard et al. | |
| 2007/0261487 | A1 | 11/2007 | Sintes et al. | |
| 2008/0066741 | A1 * | 3/2008 | LeMahieu | A61M 11/041 128/200.21 |
| 2008/0191148 | A1 * | 8/2008 | Gibson | B65B 3/003 250/432 PD |
| 2009/0246085 | A1 * | 10/2009 | Watson | B01L 3/0293 422/400 |
| 2013/0192623 | A1 | 8/2013 | Tucker et al. | |
| 2013/0306084 | A1 | 11/2013 | Flick | |
| 2014/0096781 | A1 | 4/2014 | Sears et al. | |
| 2016/0366946 | A1 * | 12/2016 | Murison | A24F 15/12 |
| 2017/0027229 | A1 * | 2/2017 | Cameron | H04L 67/04 |
| 2019/0037766 | A1 * | 2/2019 | Schrader | A01C 23/024 |
| 2019/0263680 | A1 * | 8/2019 | Dobrinsky | C02F 1/325 |

FOREIGN PATENT DOCUMENTS

| | | |
|---|---|---|
| CN | 203037314 U | 7/2013 |
| CN | 103808832 A | 5/2014 |
| CN | 103889488 A | 6/2014 |
| CN | 104106844 A | 10/2014 |
| CN | 203873007 U | 10/2014 |
| CN | 203952437 U | 11/2014 |
| CN | 203981244 U | 12/2014 |
| DE | 202012004792 U1 | 6/2012 |
| JP | 2014029278 A | 2/2014 |
| TW | 201425882 A | 7/2014 |
| WO | 9920132 A1 | 4/1999 |
| WO | 2007138247 A1 | 12/2007 |
| WO | 2013116558 A1 | 8/2013 |
| WO | 2014027561 A2 | 2/2014 |

OTHER PUBLICATIONS

Patent Cooperation Treaty, International Search Report, Application No. PCT/CN2014/094908, dated Oct. 8, 2015.
Patent Cooperation Treaty, Written Opinion, Application No. PCT/CN2014/094908, dated Oct. 8, 2015.
United Kingdom Intellectual Property Office, Combined Search and Examination Report, Application No. GB 1502498.7, dated Mar. 30, 2015.
State Intellectual Property Office, First Office Action for Chinese Application No. 201480084396.0; dated Jun. 3, 2019; 13 pages.
CNIPA, Second Office Action for Chinese Patent Application No. 201480084396.0. dated Apr. 2, 2020. 9 pages with English summary.

* cited by examiner

ELECTRONIC CIGARETTE LIQUID DETECTION AND MEASUREMENT SYSTEMS

RELATED APPLICATION

This Application is a U.S. National Phase Application of International Patent Application No. PCT/CN2014/094908, filed Dec. 25, 2014.

BACKGROUND OF THE INVENTION

An electronic cigarette or similar vaporization device includes a liquid, referred to as e-liquid, which is vaporized or atomized in an atomizer. Using an e-liquid that is not suitable for the vaporization device may cause overheating or underheating of the e-liquid, or other improper operations. Thus, there is a need to prevent use of unsuitable e-liquids in the device.

SUMMARY OF THE INVENTION

An electronic cigarette or similar vaporization device has an e-liquid detection system which can verify that the e-liquid is acceptable for use in the device. The system may detect one or more indicators, and/or physical or chemical properties of the e-liquid. The system may also measure the e-liquid level in the device.

BRIEF DESCRIPTION OF THE DRAWINGS

In the drawings, the same reference number indicates the same element in each of the views.

DETAILED DESCRIPTION

A vaporization device has an e-liquid detection system, a liquid storage element containing an e-liquid, and an atomizer. The vaporization device may be an electronic cigarette, electronic pipe, or electronic cigar, or any device that vaporizes a liquid for inhalation. The liquid storage may be at least part of an e-liquid cartridge or a so-called e-liquid cartomizer, clearomizer or tankomizer.

The-liquid detection system may verify that the e-liquid in the vaporization device is suitable for use in the device and prevent unauthorized refilling and/or modifications of the e-liquid by the user. The atomizer may be configured to shut down if the e-liquid detection system does not provide a signal of acceptance. In certain embodiments, the e-liquid detection system may also determine the e-liquid level in the liquid storage.

The liquid storage element stores a majority amount (e.g., about 95% to about 99.9%, or about 95% to about 99%) of the e-liquid contained in the device. Thus, measuring the e-liquid level in the liquid storage is substantially equivalent to measuring the e-liquid level in the device. As used herein, the term "about" followed by a numeral means a range of the numeral ±5% or 10% of the numeral.

The liquid storage element may take any shape as desired. For example, the liquid storage element may be a tube, tank, bottle or container containing the e-liquid. The liquid storage element may contain an absorbent or porous filler material.

Figure 1:
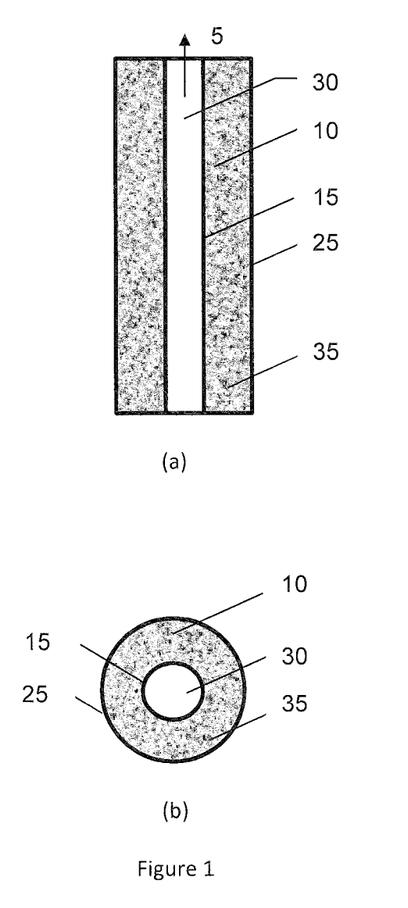
FIG. 1 shows a section view (a) and a top view (b) of an example of a liquid storage.

FIG. 1 shows a section view (a) and a top view (b) of an example of a liquid storage element 10 having a through hole 30 extending along the direction of the air flow 5. In certain embodiments, the liquid storage 10 has a first wall 15 and a second wall 25, with the through hole 30 in the first wall 15. The first and second walls 15 and 25 together form a compartment 35 that holds the e-liquid. In certain embodiments, the liquid storage element may have an absorbent material, optionally forming the through hole 30, confined by the second wall 25, with no first wall 15 needed. In other embodiments, the liquid storage element is hollow or open, and contains no solid materials.

The entire inner wall of the liquid storage element, or one or more parts of it may be polished, or coated with a layer (e.g. film, coating, etc.) reflective to light and/or sonic signals. For example, the sidewall and the bottom of the liquid storage element may be polished or coated with a reflective layer.

Fluorescent e-liquid Detection System

One aspect of the invention relates to a vaporization device comprising a liquid storage element storing an e-liquid, a fluorescent e-liquid detection system, and an atomizer. The fluorescent e-liquid detection system has a light source and a light detector. The e-liquid contains at least one product indicator. The light source provides a first light that is absorbed by the product indicator, with the product indicator emitting a second light that is detected by the light detector. For a known product indicator, the wavelengths of the first and the second lights are also known. The absence of the second light of the second pre-determined wavelength indicates the absence of the pre-determined product indicator. Thus, the atomizer may be configured to shut down when the light detector does not receive the second light of the second pre-determined wavelength.

Examples of product indicators are fluorophores that emit light of longer wavelengths (fluorescent light) than the light absorbed (absorbent light). Preferred product indicators only emit fluorescent light when being exposed to the absorbent lights. Examples of fluorophores are, compounds having a conjugated system (e.g. single bond-double bond conjugate system(s), aromatic system(s) further conjugated with double bond(s) and/or other aromatic system(s)). Quinine may be used as a product indicator. Quinine is inexpensive, highly sensitive, and safe for human consumption. It is included in the World Health Organization's list of essential medicines, a list of the most important medications needed in a basic health system. Other examples of fluorophores suitable for product indicators include Alexa Fluor dyes (e.g.

Alexa Fluor 488 and 514), BODIPY dyes (e.g. BODIPY FL, BODIPY R6G, 8-phenyl BODIPY), cyanine dyes (e.g. Cy 5.5, and Cy 7), cypate, fluorescein, indocyanine green (ICG), Oregon green dyes (e.g., Oregon green 488, Oregon green 514), rhodamine dyes (e.g. rhodamine 110, rhodamine 6G, and rhodamine X), rhodol, TAMRA (5-(and-6)-carboxytetramethylrhodamine), Texas red, and xanthene derivatives (e.g. Tokyo green).

The concentration of the product indicator(s) in a suitable e-liquid is advantageously as low as possible. In e-liquids suitable for use in an electronic cigarette, the concentration of product indicator may be at or close to the threshold of detection. The e-liquid will then be suitable or useable as is, but become non-suitable if diluted, thereby preventing use of unapproved e-liquid mixtures. Most of the fluorophores may be used at a very lower concentration without recognizable toxic effect.

Examples of light sources are UV LED, or any light source that provides the suitable absorbent light. As used herein, the wavelength specified for an absorbent light for a fluorophore is the wavelength at the maximum absorption. The fluorophore may be properly excited by lights in a wavelength range of the maximum absorption ±10 nm, ±20 nm, ±50 nm, ±100 nm, or ±200 nm. For example, the maximum absorption wavelength for quinine is about 560 nm. A light source in the wavelength of 550 nm to 570 nm, 5400 nm to 580 nm, or 510 nm to 610 nm will be suitable to excite quinine. The maximum absorption wavelength of some other fluorophore examples is about 346 nm to about 782 nm for the Alexa Fluor dyes (e.g. about 495 nm for Alexa Fluor 488, about 517 nm for Alexa Fluor 514), about 500 nm to about 646 nm for BODIPY dyes (e.g. about 503 for BODIPY FL, about 528 for BODIPY R6G, and about 524 for 8-phenyl BODIPY), about 489 nm to about 743 nm for cyanine dyes (e.g. about 675 nm for Cy 5.5, and about 743 nm for Cy 7), about 494 nm for fluorescein, about 600 nm to about 900 nm for ICG (e.g., about 800 nm), about 490 nm to about 515 nm for Oregon green dyes (e.g., about 496 nm for Oregon green 488, about 511 nm for Oregon green 514), about 528 nm to about 586 nm for rhodamine dyes (e.g. about 498 nm for rhodamine 110, about 530 nm for rhodamine 6G, and about 585 nm for rhodamine X), about 492 nm for rhodol, about 557 nm for TAMRA, about 589 nm for Texas red, and about 491 nm for xanthene derivatives such as Tokyo green.

Examples of light detectors are photodetectors having a color filter to filter only the indicator fluorescent light to the detector (e.g., green (about 460 nm) for quinine; about 442 nm to about 805 nm for the Alexa Fluor dyes (e.g. about 519 nm for Alexa Fluor 488, about 542 nm for Alexa Fluor 514); about 506 nm to about 660 nm for BODIPY dyes (e.g. about 512 for BODIPY FL, about 550 for BODIPY R6G, and about 540 for 8-phenyl BODIPY); about 506 nm to about 767 nm for cyanine dyes (e.g. about 694 nm for Cy 5.5, and about 767 nm for Cy 7); about 524 nm for fluorescein; about 750 to about 950 nm for ICG (e.g., about 810 nm and about 830 nm); about 520 nm to about 535 nm for Oregon green dyes (e.g., about 524 nm for Oregon green 488, about 530 nm for Oregon green 514); about 553 nm to about 605 nm for rhodamine dyes (e.g. about 520 nm for rhodamine 110, about 566 nm for rhodamine 6G, and about 597 nm for rhodamine X); about 516 nm for rhodol; about 583 nm for TAMRA; about 615 nm for Texas red; and about 510 nm for xanthene derivatives such as Tokyo green.

The light source may be configured to flash at a first puff to verify the e-liquid as a suitable e-liquid. If the e-liquid does not fluoresce, the vaporization device may shut down.

The light source may be programmed to flash at programmed intervals to determine the e-liquid level according to the intensity of fluorescent light the light detector detects, and the refractive index of the e-liquid. A table or plot of the parameter (e.g. refractive index) detected v. remaining e-liquid level may be obtained for a specific type of e-liquid and e-liquid detection system. Then, the table or plot may be used to determine the corresponding e-liquid level for a measured parameter.

The results may be displayed on the vaporization device to indicate the e-liquid level. For example, an LED showing different colors may be used to indicate the e-liquid level (e.g. red: empty; green: full; amber: medium); or a digital display may be used to show the e-liquid level.

Figure 2:
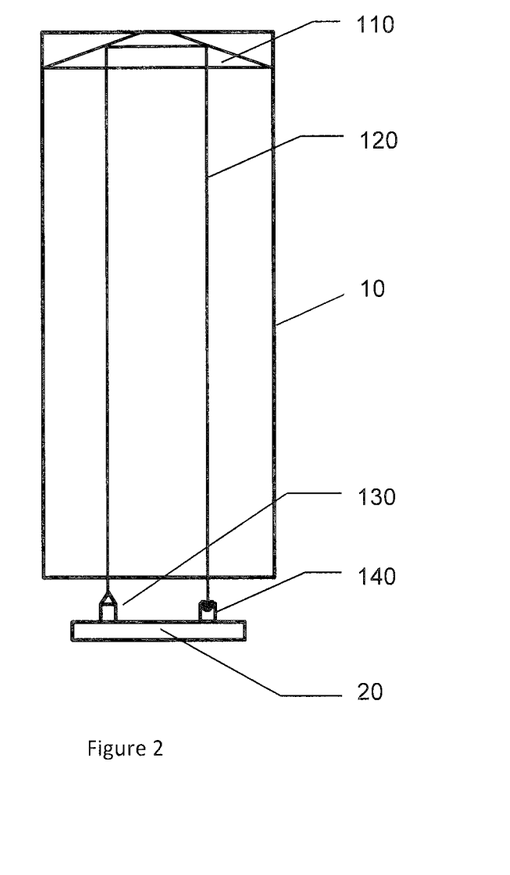
FIG. 2 shows a section view of an example of a fluorescent e-liquid detection system.

FIG. 2 shows a section view of an example of a fluorescent e-liquid detection system for a liquid storage 10. A prism 110 is placed on one end of the liquid storage 10. Alternatively, the prism 110 may be omitted if the inner surface of said end of the liquid storage 10 reflects light sufficiently well. A light source (e.g. a LED) 130 and a light detector 140 are placed in proximity to the other end of the liquid storage 10. The e-liquid in the liquid storage 10 comprises a product indicator. The product indicator absorbs the light provided by the light source 130 and emits a fluorescent light received by the light detector 140, as shown by the light path 120 in FIG. 2.

Figure 3:
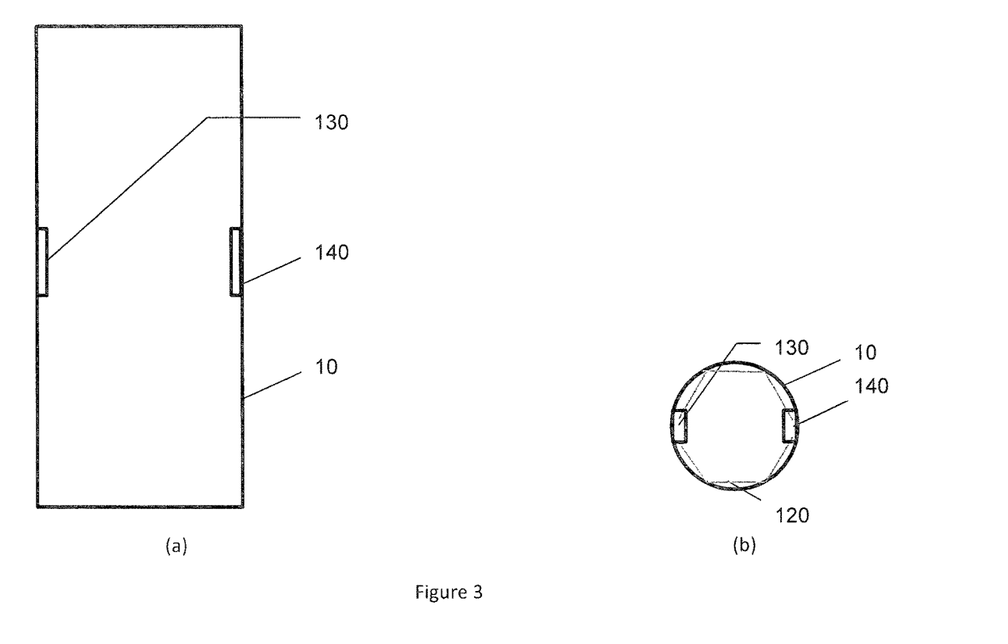
FIG. 3 shows a section view (a) and a top view (b) of another example of a fluorescent e-liquid detection system.

FIG. 3 shows a section view (a) and a top view (b) of another example of a fluorescent e-liquid detection system. The inside of the liquid storage 10 is polished and may reflect light as shown by the light path 120 in the top view of the fluorescent e-liquid detection system (FIG. 3b). The light source (e.g. a LED) 130 and the light detector 140 are placed on the inside wall of the liquid storage 10, such that the light detector 140 receives the fluorescent light the product indicator emits upon absorbance of the light provided by the light source 130.

Figure 4:
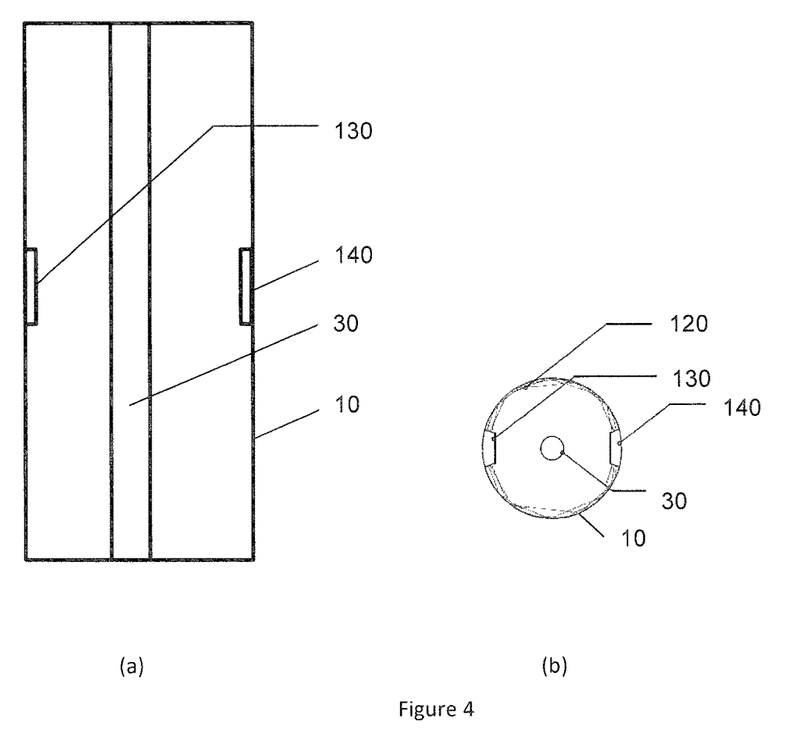
FIG. 4 shows a section view (a) and a top view (b) of another example of a fluorescent e-liquid detection system.

FIG. 4 shows a section view (a) and a top view (b) of another example of a fluorescent e-liquid detection system for a liquid storage 10, wherein the liquid storage 10 has a through hole 30 as described supra (see FIG. 1). The inside of the liquid storage 10 is polished and may reflect light as shown by the light path 120 in the top view of the fluorescent e-liquid detection system (FIG. 4b). The light source (e.g. a LED) 130 and the light detector 140 are placed on the inside wall of the liquid storage 10, such that the light detector 140 receives the fluorescent light the product indicator emits upon absorbance of the light provided by the light source 130.

Figure 5:
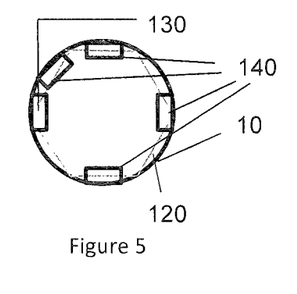
FIG. 5 shows a section view (a) and a top view (b) of an example of the capacitor e-liquid detection system.

The light source 130 and the light detector 140 are shown to be on about the opposite side of the liquid storage 10 in FIGS. 3 and 4. However, the light detector may be placed at any position (e.g., other positions shown in FIG. 5) in the liquid storage 10 as long as it can receive the fluorescent light.

Figure 6:
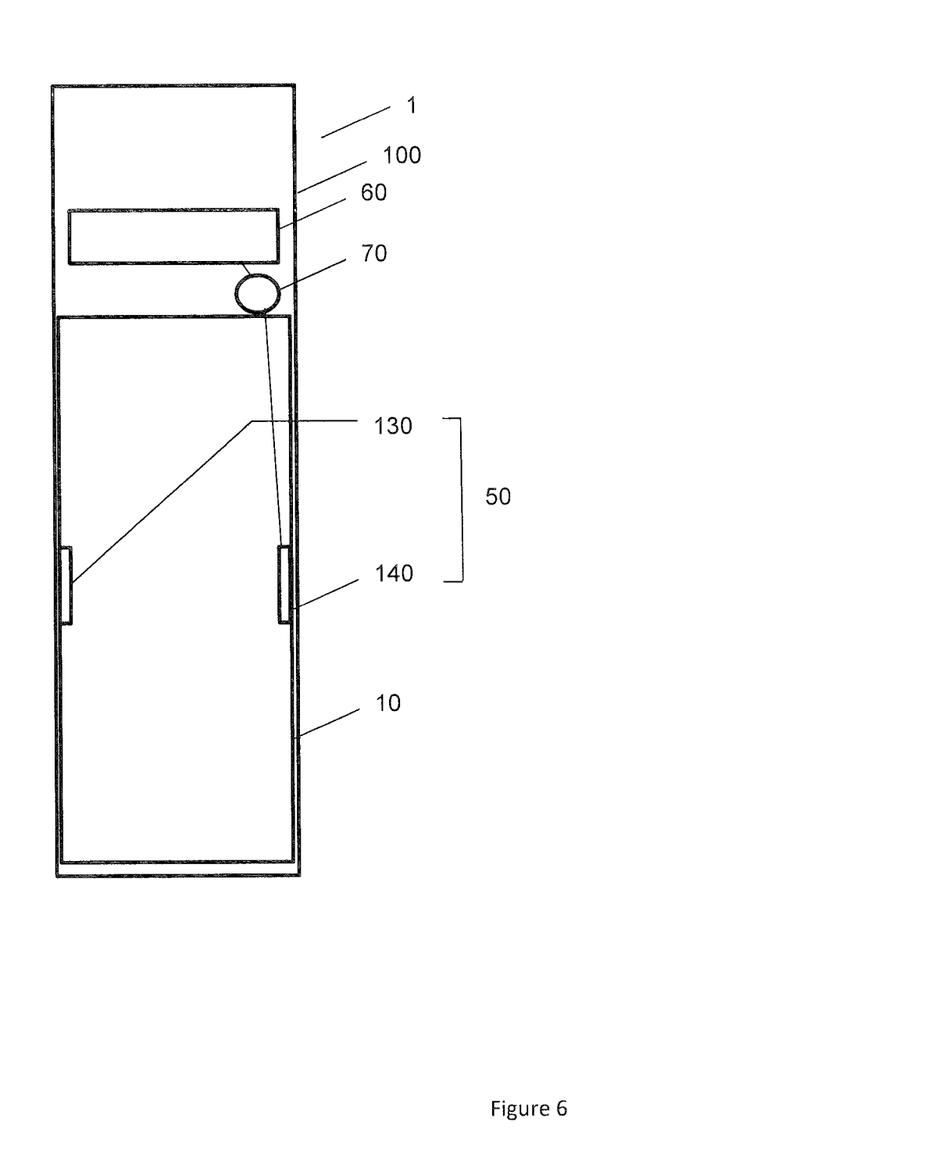
FIG. 6 shows a section view of an example of an electronic cigarette comprising an e-liquid detection system.

FIG. 6 shows a section view of an electronic cigarette 1 having a tubular housing 100, with a liquid storage element 10, an e-liquid detection system 50, and an atomizer 60 in the housing 100. The e-liquid detection system 50 includes a light source 130 positioned to emit light into the liquid storage element 10 and a light detector 140 positioned to detect light emitted from the light source 130 into the liquid storage element 10. A controller 70 in the housing 100 electrically is connected to the e-liquid detection system 50 and to the atomizer 60, with the controller 70 allowing activation of the atomizer 60 based on a signal from the liquid detection system 50.

The light detector 140 in the electronic cigarette 1 is positioned to detect light reflected off of a surface of the liquid storage element 10 (e.g., as shown in FIGS. 3b and 4b).

The light detector 140 in the electronic cigarette 1 is positioned to detect light passing through the liquid storage element 10 (e.g., as shown in FIGS. 3b and 4b).

Capacitor e-liquid Detection System

Another aspect of the invention relates to a vaporization device comprising a liquid storage storing an e-liquid, a capacitor e-liquid detection system, and an atomizer.

The capacitor e-liquid detection system comprises a first conductor and a second conductor. The first and second conductors are at least partially parallel to each other, and configured to form a capacitor circuit having a capacitance. The first and second conductors extend from one end of the liquid storage substantially to the other end thereof through the longitude direction thereof. The first and second conductors are configured such that a substantial amount (e.g., about 90% to about 99.9%, about 95% to about 99.9%, about 90% to about 95%, or about 95% to about 99%) of the e-liquid in the liquid storage is between the first and second conductors. Thus, the permittivity of the capacitor relates to a substantial amount (e.g., about 90% to about 99.9%, about 95% to about 99.9%, about 90% to about 95%, about 95% to about 99%) of the e-liquid remained in the liquid storage.

Figure 7:
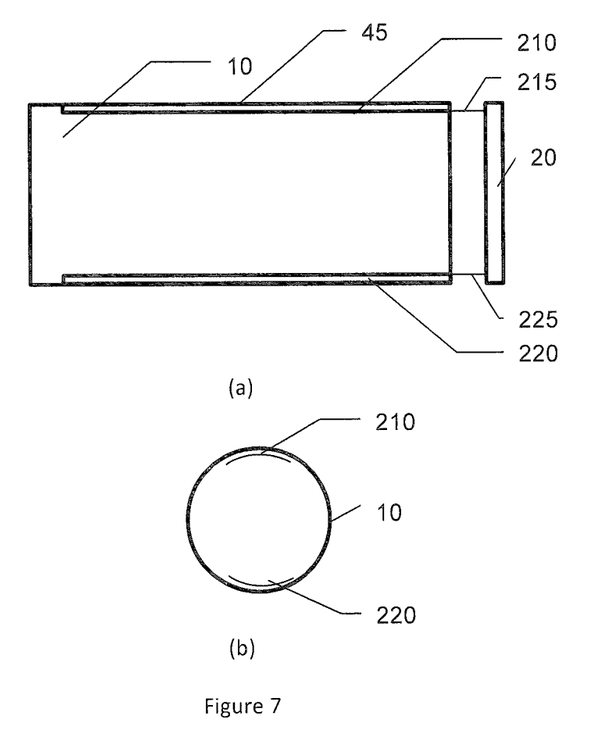
FIG. 7 shows a section view (a) and a top view (b) of another example of the capacitor e-liquid detection system.

The liquid storage 10 may be a tube as shown in FIG. 7. FIG. 7 shows a section view (a) and a top view (b) of an example of the capacitor e-liquid detection system. The first conductor 210 and the second conductor 220 may be conductive plates (e.g. metal plates). The first and second conductors 210 and 220 are configured to be as close to the outside wall 45 of the liquid storage 10 as possible to maximize the amount of e-liquid positioned between the first and the second conductors 210 and 220. The first and the second conductors 210 and 220 are at least partially parallel to each other, e.g., about 80% to about 99.9%, about 90% to about 99.9%, about 95% to about 99.9% of the area of the first conductor 210 is parallel to the second conductor 220. The first and the second conductors 210 and 220 are configured to form a capacitor circuit having a capacitance. One end of the first and the second conductors 210 and 220 are electronically connected to the PCB 20 (outside of the liquid storage 10) via a first lead 215 and a second lead 225, respectively. The other end of the first and the second conductors 210 and 220 are not electronically connected.

Figure 8:
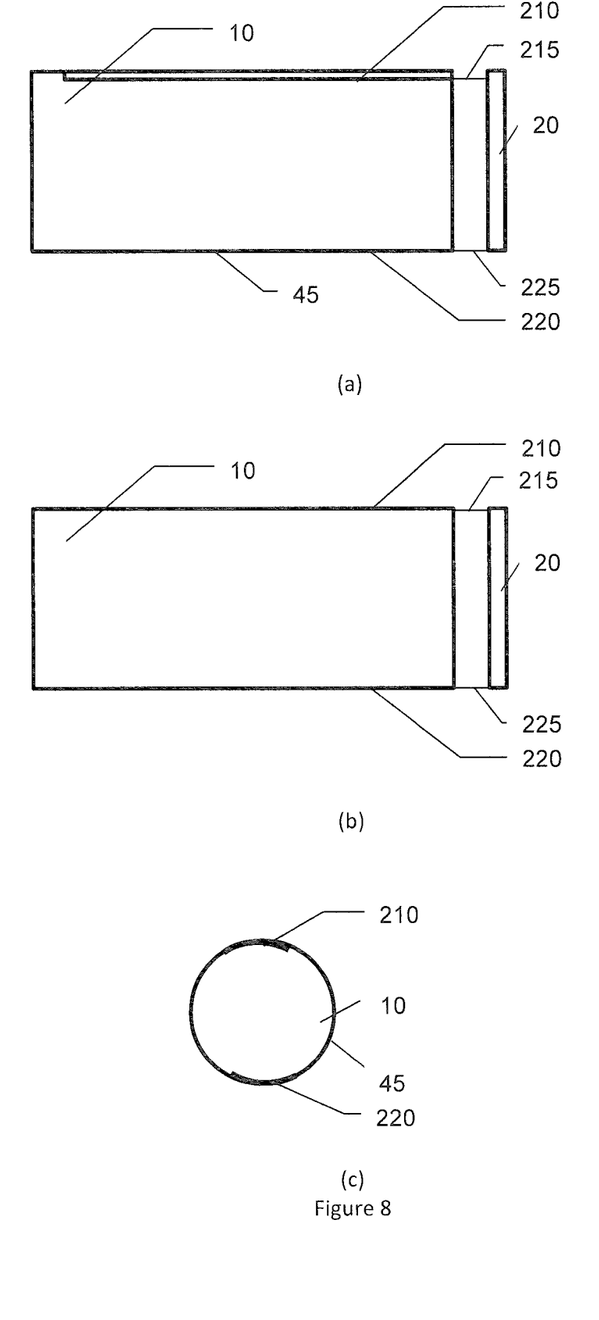
FIG. 8 shows a section view (a) of another examples of the capacitor e-liquid detection system; and a section view (b) and a top view (c) of yet another examples of the capacitor e-liquid detection system.

FIG. 8(a) shows a section view of another example of the capacitor e-liquid detection system disclosed herein. At least a portion of the outside wall 45 of the liquid storage 10 is conductive (e.g. metal) and at least partially parallel to the first conductor 210. Thus, the portion of the outside wall 45 may serve as the second conductor 220. One end of the first and the second conductors 210 and 220 may be electrically connected to the PCB 20 (outside of the liquid storage 10) via a first lead 215 and a second lead 225, respectively. The other end of the first and the second conductors 210 and 220 are not electrically connected.

FIG. 8(b) shows a section view and FIG. 8(c) shows a top view of another example of the capacitor e-liquid detection system disclosed herein. Two separate conductive (e.g. metal) portions of the outside wall 45 of the liquid storage 10 that are insulate from each other, are at least partially parallel to each other. Thus, the two separate conductive portions of the outside wall 45 may serve as the first and the second conductors 210 and 220, respectively. The first and the second conductors 210 and 220 are configured to form a capacitor circuit having a capacitance, as described supra.

One end of the first and the second conductors 210 and 220 may be electronically connected to the PCB 20 (outside of the liquid storage 10) via a first lead 215 and a second lead 225, respectively. The other end of the first and the second conductors 210 and 220 are not electronically connected.

The first and/or the second conductors may adopt various widths. The parallel portion of the first and second conductors 210 and 220 may be narrow or broad. The first and/or second conductors 210 and 220 may be relatively broad and extend along partial of or substantially (e.g., about) the whole circumference of the wall(s) of the liquid storage 10 (e.g., see FIG. 9 for conductors surrounding the circumference of the walls of the liquid storage 10).

The liquid storage may comprise a through hole 30 as described supra (FIG. 1). The liquid storage 10 comprises a first wall 15 and a second wall 25.

Figure 9:
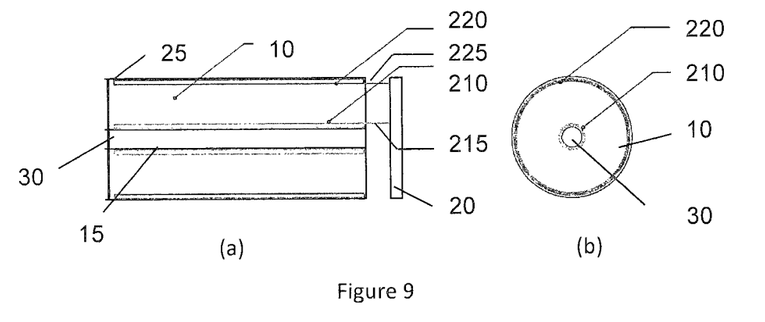
FIG. 9 shows a section view (a) and a top view (b) of another example of the capacitor e-liquid detection system.

FIG. 9 shows a section view (a) and a top view (b) of an example of the capacitor e-liquid detection system disclosed herein. The first and the second conductors 210 and 220 are conductive plates surrounding the first wall 15 and the second wall 25 of the liquid storage 10, respectively. Alternatively, the first and the second conductors 210 and 220 may only extend along part of the circumferences of the first and the second walls 15 and 25, respectively, as long as the conductors 210 and 220 are at least partially parallel to each other. The first and the second conductors 210 and 220 are configured to form a capacitor circuit having a capacitance, as described supra. One end of the first and the second conductors 210 and 220 may be electrically connected to the PCB 20 (outside of the liquid storage 10) via a first lead 215 and a second lead 225, respectively. The other end of the first and the second conductors 210 and 220 are not electrically connected.

In another embodiment, the first wall 15 is conductive (e.g., metal) and may serve as the first conductor 210. In another embodiment, the second wall 25 is conductive (e.g., metal) and may serve as the second conductor 220. In another embodiment, both of the first and the second walls 15 and 25 are conductive (e.g., metal) and serve as the first and the second conductors 210 and 220, respectively.

For a capacitor having a media (e.g., e-liquid) between the first and second conductors thereof, the permittivity of the capacitor depends on the amount and the composition of the liquid. The more sensitive the permittivity changes over the liquid amount, the more accurate the capacitor e-liquid detection system may determine whether the e-liquid is a suitable product, and/or the remaining e-liquid level. Substances having higher permittivity may increase the sensitivity of permittivity changes to change of the liquid amount. Preferred examples include, without limitation, glycerol.

An e-liquid comprising compatible high permittivity substances may be used to identify suitable product and determine the remaining e-liquid level.

A table or plot of the parameter (e.g. permittivity) detected v. remaining e-liquid level may be obtained for a specific type of e-liquid and e-liquid detection system. Then the table or plot may be used to determine the corresponding e-liquid level for a measured parameter.

In certain embodiments, the capacitor e-liquid detection system may be configured to measure the permittivity at programmed intervals to determine the permittivity change pattern of the e-liquid. The vaporization device may shut down if the permittivity change pattern measured is significantly different (e.g. smaller) from what is expected from using a suitable product. The results of remaining e-liquid level may be displayed on the surface of the vaporization device as described supra.

Ultrasound e-liquid Detection System

An ultrasound e-liquid detection system may be used. The ultrasound e-liquid detection system has an ultrasound emitter and an ultrasound detector. When an ultrasound signal is applied to a liquid, the resonant frequency received depends on the amount of the liquid in the container. When a sonar signal is applied to the liquid storage, the resonant frequency received reflects the remaining e-liquid level in the liquid storage element.

Figure 10:
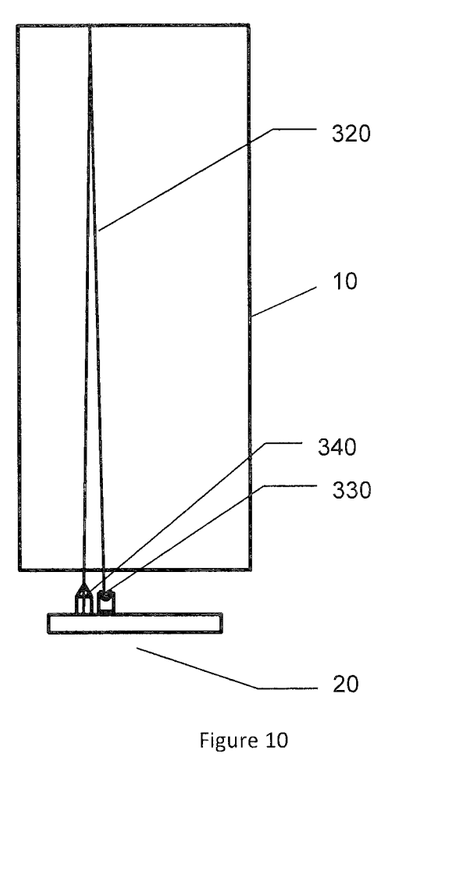
FIG. 10 shows a section view of an example of an ultrasound e-liquid detection system and the ultrasonic path.

FIG. 10 shows a section view of an example of an ultrasound e-liquid detection system and the ultrasonic path. The ultrasound emitter 330 and the ultrasound detector 340 are placed in proximity to one end of the liquid storage 10. The inner surface of the other end of the liquid storage 10 is reflective to sonar signals. The ultrasound detector 340 is positioned to receive the sonar signal after it travels through the liquid storage 10, via the ultrasonic path 320.

A table or plot of the parameter (e.g. sonar signals) detected v. remaining e-liquid level may be obtained for a specific type of e-liquid and e-liquid detection system. Then the table or plot may be used to determine the corresponding e-liquid level for a measured parameter. In certain embodiments, the ultrasound e-liquid detection system may be configured to measure the resonant frequency at programmed intervals to determine the resonant frequency of the e-liquid. The results of remaining e-liquid level may be displayed on the surface of the vaporization device as described supra.

Pressure e-liquid Detection System

Figure 11:
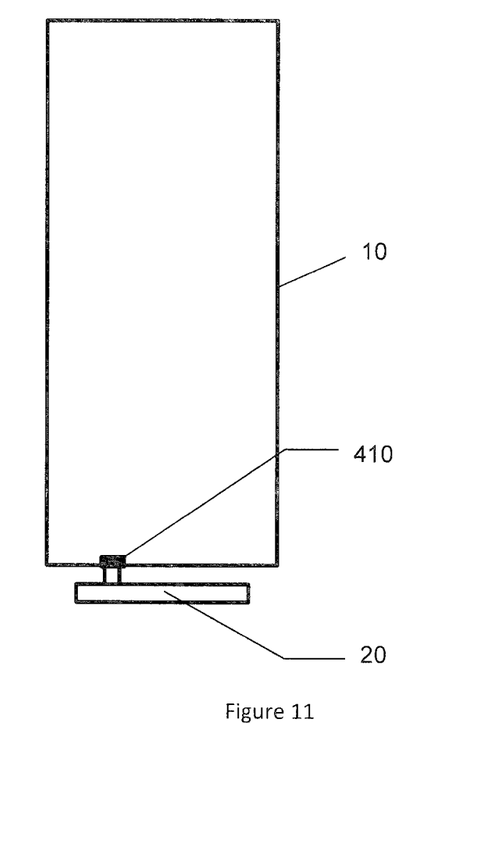
FIG. 11 provides a section view of an example of the pressure e-liquid detection system.

Another aspect of the invention relates to a vaporization device comprising a liquid storage storing an e-liquid, a pressure e-liquid detection system, and an atomizer. The pressure e-liquid detection system comprises a pressure sensor positioned at one end of the liquid storage that is closer to the direction of gravity. The weight of the liquid storage will change based on the e-liquid level therein. Because the pressure measured by the pressure sensor relates to the weight of the liquid storage, measuring the pressure may determine the remaining e-liquid level in the liquid storage. FIG. 11 provides a section view of an example of the pressure e-liquid detection system. The pressure sensor 410 is positioned in proximity to one end of the liquid storage 10 that is close to the PCB 20.

A table or plot of the parameter (e.g. pressure) detected v. remaining e-liquid level may be obtained for a specific type of e-liquid and e-liquid detection system. Then the table or plot may be used to determine the corresponding e-liquid level for a measured parameter. In certain embodiments, the pressure e-liquid detection system may be configured to measure the pressure at programmed intervals to determine the pressure of the e-liquid. The results of remaining e-liquid level may be displayed on the surface of the vaporization device as described supra.

The invention claimed is:

1. A vaporization device comprising:
a tubular housing;
a liquid storage element, an e-liquid detection system, and an atomizer in the housing, with the e-liquid detection system including a light source positioned to emit light of a first wavelength into an e-liquid in the liquid storage element and a light detector positioned to detect light of a second wavelength emitted by the e-liquid; and
a controller in the housing electrically connected to the e-liquid detection system and to the atomizer, with the controller allowing activation of the atomizer based on the light detector detecting light of the second wavelength.

2. The vaporization device of claim 1 with the light detector positioned to detect light reflected off of a surface of the liquid storage element.

3. The vaporization device of claim 1 with the light detector positioned to detect light passing through the liquid storage element.

4. The vaporization device of claim 1 wherein the light of the second wavelength is a fluorescent light emitted by a product indicator when exposed to the light of the first wavelength.

5. The vaporization device of claim 1 wherein:
the light source is positioned in proximity to a first end of the liquid storage element; and the vaporization device further comprises a prism positioned at a second end of the liquid storage element.

6. The vaporization device of claim 5 wherein:
the light source is positioned in proximity to a first end of the liquid storage element; and an inner surface of the second end of the liquid storage element reflects light from the light source.

7. The vaporization device of claim 1 wherein the light source is positioned on an inner surface of the liquid storage element.

8. The vaporization device of claim 1 wherein the light detector comprises one or more photodetectors that can detect the light of the second wavelength.

9. The vaporization device of claim 8 further including a filter provided with the one or more photodetectors, the filter passing only the light of the second wavelength.

10. The vaporization device of claim 1 with the e-liquid including a fluorophore as a product indicator.

11. The vaporization device of claim 1 with the e-liquid containing a product indicator selected from the group consisting of Alexa Fluor dyes, BODIPY dyes, cyanine dyes, cypate, fluorescein, indocyanine green (ICG), Oregon green dyes, rhodamine, rhodol, TAMRA (5-(and-6)-carboxytetramethylrhodamine), Texas red, and xanthene derivatives.

12. The vaporization device of claim 9 wherein:
the e-liquid contains quinine; the first wavelength is about 560 nm; and the second wavelength is about 460 nm.

13. The vaporization device of claim 1 wherein the e-liquid comprises quinine.

14. The vaporization device of claim 13 wherein the e-liquid further comprises propylene glycol (PG), glycerin (G), and/or polyethylene glycol 400.

15. A vaporization device comprising:
a housing;
a liquid storage element, an e-liquid detection system, and an atomizer in the housing, with the e-liquid detection system including a light source positioned to emit light of a first wavelength into an e-liquid in the liquid storage element and a light detector positioned to detect light of a second wavelength emitted by the e-liquid, the light detector comprising one or more photodetectors that can detect the light of the second wavelength; and
a controller in the housing electrically connected to the e-liquid detection system and to the atomizer, with the controller allowing activation of the atomizer based on the light detector detecting light of the second wavelength.

* * * * *